United States Patent [19]

Maeda et al.

[11] Patent Number: 4,844,897
[45] Date of Patent: Jul. 4, 1989

[54] ANTI-TUMOR PROTEASE PREPARATIONS

[75] Inventors: Hiroshi Maeda, 631-3, Hotakubohon-cho, Kumamoto-shi, Kumamoto-ken; Yasuhiro Matsumura, Kumamoto; Osamu Asami, Konan; Hideyuki Tanaka, Inazawa; Ikuharu Sasaki, Aichi, all of Japan

[73] Assignees: Hiroshi Maeda, Kumamoto; Amano Pharmaceutical Co., Ltd., Nagoya, both of Japan; a part interest

[21] Appl. No.: 906,240

[22] Filed: Sep. 12, 1986

[30] Foreign Application Priority Data

Sep. 13, 1985 [JP] Japan .................. 60-201607
Aug. 7, 1986 [JP] Japan .................. 61-184126

[51] Int. Cl.$^4$ .................. A61K 37/54; C12N 9/52; C12N 9/54
[52] U.S. Cl. .................. 424/94.3; 424/94.63; 435/220; 435/221
[58] Field of Search .................. 424/94.3, 94.63, 96.64; 435/220, 221

[56] References Cited

U.S. PATENT DOCUMENTS

| | | | |
|---|---|---|---|
| 3,823,072 | 7/1974 | Hooreman | 195/103.5 R |
| 4,066,503 | 1/1978 | Bashkovich et al. | 195/62 |
| 4,079,125 | 3/1978 | Sipos | 424/32 |
| 4,495,285 | 1/1985 | Shimizu et al. | 435/215 |
| 4,514,388 | 7/1983 | Psaledakis | 424/94 |

OTHER PUBLICATIONS

Enzyme Nomenclature (1978) Academic Press (New York), pp. 314-325.
Kedar et al., in Chemical Abstracts, vol. 80, 1974, Abstract No. 2208z.
Iwai et al., in Cancer Research, vol. 44, pp. 2115-2119, (May 1984).
J. J. Marshall, et al., Preparation and Characterization of a Dextran-Trypsin Conjugate, The Journal of Biological Chemistry, 251: 1081-1087 (1976).
H. Maeda, et al., Gan to Kagaku Ryoho, 12: 773-782 (1985).
H. Maeda, et al., Tailor-Making of Protein Drugs by Polymer Conjugation for Tumor Targeting: A Brief Review on Smancs, Journal of Protein Chemistry, vol. 3, No. 2, (1984), pp. 181-193.
H. Maeda, et al., Protein Tailoring for Food and Medical Uses, pp. 353-382 (edited by R. E. Feeney & J. R. Whitaker), N.Y. (1986).

Primary Examiner—Thomas G. Wiseman
Assistant Examiner—Charles L. Patterson, Jr.
Attorney, Agent, or Firm—Wegner & Bretschneider

[57] ABSTRACT

Method of treating a tumor in a mammal comprises administering to said mammal an effective anti-tumor amount of proteases originating from microorganisms.

Method of treating a tumor in a mammal comprises administering to said mammal an effective anti-tumor amount of a protease originating from a microorganism which protease is chemically modified by one of the following procedures:
(a) coupling with a saccharide,
(b) introduction of a hydrophobic polymeric group,
(c) alteration of electric charge of the protein surface,
(d) conjugation with a low molecular weight anti-tumor agent of molecular weight less than 2,000,
(e) formation of dimer or oligomer by cross-linking of protease molecules,
(f) conjugation with a synthetic polycation,
(g) conjugation with a synthetic polyanion, and
(h) combination of the above-mentioned procedures.

Microorganism protease is chemically modified by one of the following procedures:
(a) coupling with a saccharide,
(b) introduction of a hydrophobic polymeric group,
(c) alteration of electric charge of the protein surface,
(d) conjugation with a low molecular weight anti-tumor agent of molecular weight less than 2,000,
(e) formation of dimer or oligomer by cross-linking of protease molecules,
(f) conjugation with a synthetic polycation,
(g) conjugation with a synthetic polyanion, and
(h) combination of the above-mentioned procedures.

4 Claims, 3 Drawing Sheets

ANTI-TUMOR PROTEASE PREPARATIONS

BACKGROUND OF THE INVENTION

1. Field of the Invention

This invention relates to an anti-tumor agent containing protease originating from microorganisms as an effective component, to an anti-tumor agent containing chemically modified protease originating from microorganisms as an effective component, to a chemically modified protease originating from microorganisms and to a method of using such agents.

As a result of extensive studies to prepare anti-tumor agents with less side-effects on the basis of the long experiences of the inventors in the study of anti-tumor agents, the present inventors have found, for the first time, that protease originating from microorganisms, that is, a group of substances of quite a different category in the molecular properties and mechanism of action from those of the conventional anti-tumor agents, has quite effective anti-tumor action. As a result of further studies, the present inventors have also found that anti-tumor agents containing chemically modified proteases as effective components have much better anti-tumor effect than the parent proteases.

The action of proteases and chemically modified proteases originating from microorganisms as effective components of the present anti-tumor agent are degradation of proteins and the consequent cell rupture, and thus the present anti-tumor agents have an action of a quite different category from those of the conventional anti-tumor agents.

2. Related Background Art

The present inventors have already found that the structure of blood vessels in a tumor tissue is quite different from that in the normal tissue. Furthermore, lymphatics appears inoperative in the tumor tissue. That is reflected in the behavior of a high molecular weight anti-tumor agent when it is administered into the tumor tissue. Namely, its fate is quite different from that of a low molecular weight one; the high molecular weight substance is not recovered into the blood circulation nor cleared from the lymphatic system due to its absence, thus it is retained in the tumor tissue for a prolonged time. This seems due to the fact that the high molecular weight lowers the diffusion rate of the agent and also reduces the passage into the blood vessel and consequently permeation into the blood vessels and successive recovery efficiency are lowered. Furthermore, the present inventors have already found that solid tumor sites are lacking in lymphatic vessels, whereas in the normal tissue, the lymphatic system is the main route for recovery of high molecular weight and lipid substances and microparticles in such a tissue. A tumor tissue is lacking in such a lymphatic system as described above, and thus the high molecular weight substances such as enzymes, etc. can stay at the tumor site for a prolonged time [Iwai, K. et al. Cancer Res. 44, 2115-2121 (1984); Maeda, H. et al: J. Prot. Chem., 3, 181-193 (1984); Maeda, H. and Konno, T.: Gan to Kagaku Ryoho 12, 773-782 (1985); Maeda, H. et al: Protein Tailoring for Food and Medical Uses, 353-382 Feeney, R. E. and Whitaker, J. R. ed. Marcel Dekker Inc., N.Y. (1986)].

Taking these finding into account, the present inventors have presumed that when proteases and chemically modified proteases originating from microorganisms as high molecular weight substances are injected into the site, some of them could exhibit a powerful toxicity against tumor cells for a prolonged time and remarkable anti-tumor effect could be obtained.

The anti-tumor agents so far developed are mainly low molecular weight agents usually less than 2,000 dalton, which undergo rapid diffusion, and thus their pharmacological action in the tumor tissue cannot be maintained for a prolonged time unless their systemic concentration is maintained at a very high level even if they have a potent pharmacological action. This is a disadvantage and prime cause of severe side effects.

SUMMARY OF THE INVENTION

The present inventors have made extensive studies to find an anti-tumor agent having potent anti-tumor action with prolonged duration of action and a low toxicity against normal cells, and have found that several proteases originating from microorganisms have potent anti-tumor action on experimental solid tumors on mice. It has been demonstrated through in vitro tests that the administered protease has a prolonged action on tumor sites and the cell toxicity against normal cells is much lower than against tumor cells. The present inventors have established the present invention on the basis of the foregoing finding.

In the practical use of proteinaceous chemical agents as in the present invention, it has been assumed that allergic and other immunological reactions are caused to occur at the same time, or that there may be a possibility of neutralization of the action by the appearance of antibodies. Thus, the present inventors have chemically modified the enzymes to reduce the occurrence of the reaction or to circumvent such adverse problems, and also to pursue the possibility to obtain anti-tumor agents with better pharmacological properties. The present inventors have found that the anti-tumor action can be much intensified by chemical modification of the proteases originating from microorganisms.

According to one aspect of the present invention, there is provided a method of treating a tumor in a mammal which comprises administering to said mammal an effective anti-tumor amount of proteases originating from microorganisms.

According to another aspect of the present invention, there is provided a method of treating a tumor in a mammal which comprises administering to said mammal an effective anti-tumor amount of a protease originating from a microorganism which protease is chemically modified by one of the following procedures:
(a) coupling with a saccharide,
(b) introduction of a hydrophobic polymeric group,
(c) alteration of electric charge of the protein surface,
(d) conjugation with a low molecular weight anti tumor agent of molecular weight less than 2,000,
(e) formation of dimer or oligomer by cross-linking of protease molecules,
(f) conjugation with a synthetic polycation,
(g) conjugation with a synthetic polyanion, and
(h) combination of the above-mentioned procedures.

According to still another aspect of the present invention, there are provided proteases which are chemically modified by one of the following procedures:
(a) coupling with a saccharide,
(b) introduction of a hydrophobic polymeric group,
(c) alteration of electric charge of the protein surface,
(d) conjugation with a low molecular weight anti-tumor agent of molecular weight less than 2,000, (e) formation of dimer or oligomer by cross linking of protease molecules,
(f) conjugation with a synthetic polycation,
(g) conjugation with a synthetic polyanion, and
(h) combination of the above-mentioned procedures.

DESCRIPTION OF THE PREFERRED EMBODIMENTS

Proteases originating from microorganisms as effective components of the present anti-tumor agents can be prepared by culturing microorganisms and recovering the protease from the culture medium.

In the preparation of chemically modified proteases originating from microorganisms as effective components of the present anti-tumor agent, microorganisms are first cultured and then the protease is recovered from the culture medium.

To obtain protease by culturing microorganisms, such microorganisms as *Serratia marcescens, Bacillus subtilis, Streptomyces griseus, Bacillus sp., Streptomyces sp.* etc. are cultured in a tryptosoy medium, a cornsteep liquor medium, a Waksman medium, or other appropriately adjusted media at 20° C. to 50° C., preferably at about 30° C. under aerobic conditions for 20 to 50 hours, and then the cells are separated from the culture medium by filtration or by centrifugation. Protease activity is found in the supernatant of the culture medium. The supernatant is concentrated to 2 to 20-fold concentration and then subjected to other appropriate steps as dialysis, gel filtration, ion exchange chromatography, fractional precipitation, salting-out, etc., whereby purified protease having a purity of 95% or higher can be obtained. All these proteases having an anti-tumor action are neutral proteases originating from microorganisms. On the other hand, acidic protease produced by *Acrocylindrium sp.* shows an adverse effect of promoting propagation of tumors, and the activities of trypsin, chymotrypsin, and pepsin of animal origin, and papain, etc. of plant origin are completely inhibited by protease-inhibiting substances in vivo, such $\alpha_1$ antitrypsin, $\alpha_2$ antichymotrypsin, $\alpha_2$ macroglobulin, etc. These substances have no anti-tumor action.

By the chemical modification of these alkaline or neutral proteases originating from microorganisms, any one of the aforegoing proteases originating from microorganisms can be used equivalently, but in the present invention particularly, proteases originating from *Serratia marcescens* and *Bacillus sp.* are used as suitable examples.

Procedures for preparing protease originating from *Serratia marcescens* (which will be hereinafter referred to as "56K protease") and protease originating from *Bacillus sp.* (which will be hereinafter referred to as "AT protease") will be given in Preparatory Examples 1 and 2, respectively.

Preparatory Examples, Test Examples and Examples of the present anti-tumor agents containing proteases originating from microorganisms as effective components will be given below.

Preparatory Example 1

Figure 1:
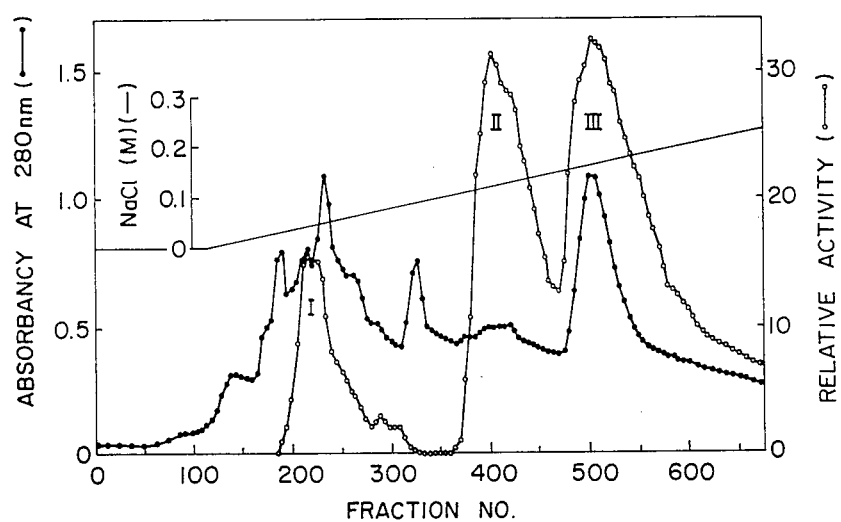
FIG. 1 shows a DEAE-cellulose column elution pattern in the purification step of 56K protease originating from *Serratia marcescens*.

*Serratia marcescens* Kums 3958 FERM-BP No. 1159 (a strain isolated from a patient suffering from human cornea ulcer and deposited as an access number 8436 in the Fermentation Research Institute) was cultured in a tryptosoy liquid medium overnight; 2 ml of the medium was inoculated on 200 to 350 ml of the same medium contained in a one liter Sakaguchi flask, and cultured at 30° C. with shaking (1–2 Hz). 25 to 30 hours thereafter, when the protease activity reached a maximum equilibrium value, the culture medium was separated into a filtrate and cells, and the filtrate was concentrated 4-fold at below 30° C. under reduced pressures, or concentrated as precipitates by addition of solid ammonium sulfate to a final saturation of 90%. Then, the concentrate was dialyzed against distilled water in the conventional manner at 4° C. for 48 to 72 hours, and the dialysate was freeze dried. The dried product was further applied to and eluted from a DEAE-cellulose column (column size: 4×40 cm) using 0.01M tris-hydrochloride buffer (pH 8.3) at a NaCl concentration gradient. The elution pattern is shown in FIG. 1.

The protease activity was measured by caseinolytic activity and the fluorescence polarization developed by the present inventors [Maeda, H.: Anal. Biochem. 92, 222–227 (1979)].

Figure 2:
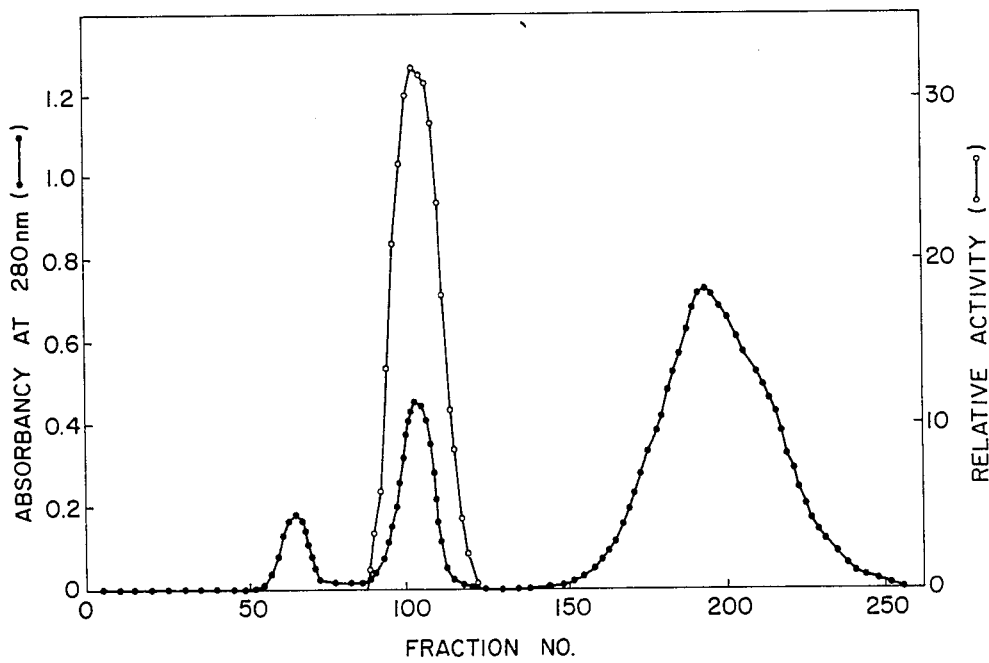
FIG. 2 shows a similar Sephadex G-100 elution pattern.

The eluted fractions were further subjected to dialysis, freeze drying, and chromatographic separation using Sephadex G-100, whereby protease of higher purity could be obtained. The elution pattern is shown in FIG. 2.

Above obtained protease, when subjected to electrophoresis in 7.5% polyacrylamide gel in the presence of 0.1% Na dodecylsulfate, showed a single band, and was named "56K protease" by the present inventors. Enzymochemical properties of 56K protease are disclosed by the present inventors and Matsumoto et al in J. Bacteriol. 157, (1) 225–232 (1984).

The toxicity of various proteases against cultured cells, influences of serum on the cell toxicity, anti-tumor action against ascitic tumor cell, effectiveness in solid tumor of mice, acute lethal toxicity test, etc. will be described below for the proteases originating from microorganisms.

Test Example 1

Cell toxicity of various proteases against cultured cells and influences of serum on the cell toxicity:

It is a requisite that the proteases serving as anti-tumor agents must be resistant to the various protease-inhibiting components in humoral fluid existing in a significant amount in the body.

The present inventors have investigated cell-killing effects of various proteases by adding the proteases to various cultured cells, and also at the same time the effect of serum on the cytotoxicity.

A 0.5 ml aliquot of RPMI-1640 medium or Eagle's NEM medium containing 10% bovine fetal calf serum was placed in a Lab Tech plastic chamber of 8-well type, (Falcon Inc.), and suspensions of various tumor cells, each containing about $1 \times 10^4$ cells in 0.5 ml, were added thereto and cultured in an incubator at 37° C. in 5% $CO_2$ (95% being air). After 24 hours, the cells in the Lab Tech chambers were allowed to culture under three different condition. In group A, they were replaced in RPMI medium with 10% fetal calf serum containing different concentrations of test protease. In group B, the same medium with appropriate protease was used but devoid of serum; In group C, a control medium was used with 10% serum but without protease. One hour and 24 hours after the culturing cytotoxicity, observed microscopically, was determined by counting the number of cells and by morphological investigation.

The results are shown in Tables 1 and 2. As is obvious from Table 1, the cell toxicity of various proteases on serum-free media strongly appears mainly on the tumor cells, and substantially not on the normal cells. As is also obvious from Table 2, an enhancing effect by serum on the tumor cell toxicity of various proteases with time became apparent. That is, 56K protease, Subtilisin and Pronase produce considerably increased cytotoxic effects in 24-hour treatment than one-hour treatment, whereas trypsin and papain produce no substantial enhancement. This enhancement appears largely due to time dependent inactivation of serum inhibitor for protease (i.e. $\alpha_2$ macroglobulin).

TABLE 1

Toxicity of various proteases against cultured cells Minimum effective concentration when cultured in the absence of serum after 24-hour treatment (ug/ml)

|  | 56K Protease | Subtilisin | Pronase | Trypsin | Papain |
|---|---|---|---|---|---|
| (1) Tumor cell | | | | | |
| Human laryngeal carcinoma (HEp-2) | <0.025 | 0.05 | 0.1 | 1.56 | 1.60 |
| Human submaxillary gland tumor (HSG) | <0.026 | 0.004 | 0.006 | 0.39 | 0.38 |
| Cervical canal cancer (HeLa) | 0.025 | <0.025 | <0.025 | 0.78 | 0.84 |
| Burkitt's lymphoma (Raji) | 0.05* | 0.006 | 0.006 | 0.05 | 0.06 |
| Rat neuroblastoma (C6) | 0.10 | 0.20 | 0.20 | 1.56 | 1.60 |
| Mouse leukemia (RL ♂ 1) | 1.56* | <0.003 | <0.003 | 0.78 | 0.82 |
| (2) Normal cell | | | | | |
| Human fibroblast (WISH) | 3.13 | 0.31 | 0.39 | 1.56 | 1.52 |
| Monkey kidney fibroblast (Vero) | 3.13 | 1.50 | 1.56 | 1.56 | 1.58 |
| Human fetus lung fibroblast (HEL) | <0.025 | <0.025 | <0.025 | 0.20 | 0.20 |
| Human normal T-lymphocytes | 50** | 0.025 | 0.025 | 0.39 | 0.37 |
| African green monkey kidney (Epithelial cells) | 0.1 | 0.025 | 0.025 | 0.39 | 0.38 |
| Rat hepatocytes (Liver cells) | >5.0 | >5.0 | >5.0 | >5.0 | >5.0 |

*loss of clump formation
**loss of E-rosette formation

TABLE 2

Cytotoxicity induced by protease activity in the presence of serum (i.e. enhancement of the cytotoxic effect after 24-hour treatment by protease by addition of serum)
Cell (a) Cytotoxicity in the presence of serum with time (b)
(Strength for one-hour treatment)

| | 56K protease | Subtilisin | Pronase | Trypsin | Papain |
|---|---|---|---|---|---|
| HeP2 | >64 | 20 | 8 | 0-4 | 0-4 |
| HSG | 32 | 16 | 8 | 2-4 | 2-4 |
| HeLa | 32 | 12 | 8 | 2-4 | 2-4 |
| C6 | 32 | 10 | 8 | 2 | 2 |
| WISH | 16 | 10 | 8 | 4 | 2 |
| Vero | 16 | 10 | 2 | 2-4 | 2-4 |
| HEL | >4 | — | — | 2 | 2 |
| GMK | 2 | 2 | 2 | 2 | 2 |

(a) The cell origins are the same as given in Table 1.
(b) Numerals show reciprocal number of dilution for obtaining the equivalent effect after 24-hour treatment on the basis of the effect of the original protease (the effect after the one-hour treatment by protease in the presence of serum). For example, numeral 32 shows that the equivalent potency can be obtained in an amount of 1/32 for 1 hr compared with that after 24 hours even in the presence of serum.

Test Example 2

Anti-tumor actions of various proteases: Effectiveness on mouse solid tumor (i.e., effect on methylcholanthrene-induced tumor (Meth A tumor):

0.05 ml containing about $10_6^6$ Meth A tumor cells was subcutaneously inoculated on a Balb/C mouse with an injection syringe, and after about 7 to 9 days when the diameter of the respective tumors reached 8 to 10 mm in diameter, 0.1 ml each of the respective proteases dissolved at predetermined concentrations was injected into each solid tumors. The diameters of the tumors after two administrations (once for each day) were measured. The results are shown in FIG. 3.

Figure 3:
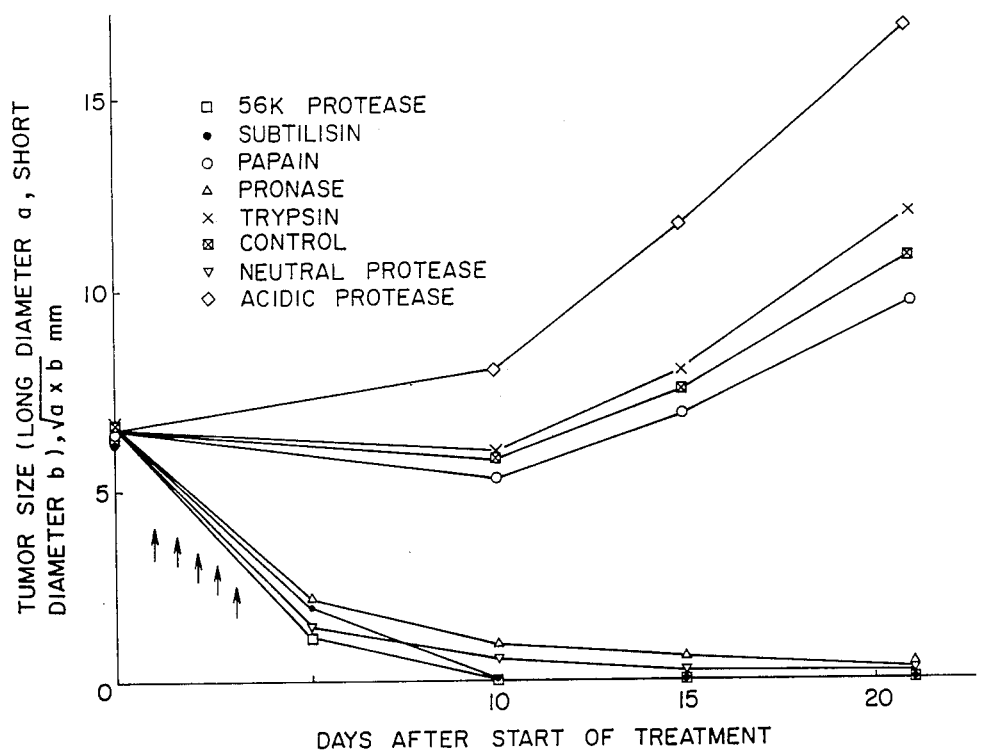
FIG. 3 shows anti-tumor actions of various proteases against Meth A tumor, where the arrow marks show administration of the proteases into tumors.

As is obvious from FIG. 3, the tumors disappeared with 4 species, i.e. 56K protease, neutral protease, Pronase and Subtilisin among the various proteases, whereas acidic protease, trypsin, pepsin and papain had no substantial action against the tumor propagation.

Test Example 3

Figure 4:
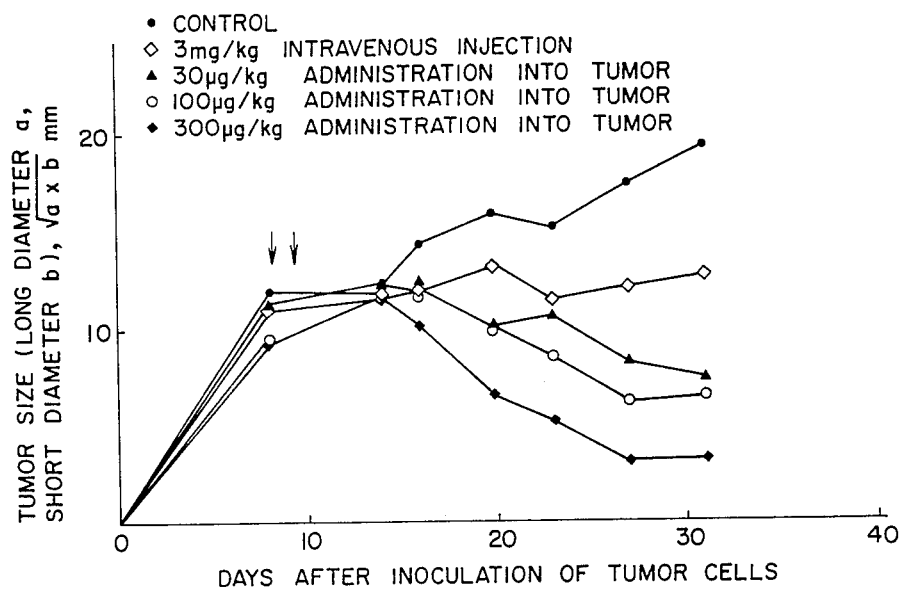
FIG. 4 shows anti-tumor actions of 56K protease against S-180 solid tumor, where arrow marks show administration of 56K protease.

Anti-tumor action of 56K protease,
(1) Anti-tumor effect on S-180:
Various amounts of 56K protease were injected into S-180 solid tumors formed on ddY mouse in the same manner as in Test Example 2 in total seven administrations, each administration being made on every two or three days, to examine the anti-tumor effect. The results are shown in FIG. 4. As is obvious from FIG. 4, administration of 30 μg/kg or more was effective, and the tumors substantially or completely disappeared with five administrations each of 300 μg/kg, and no side effect due to the administration of protease was observed at all.

Figure 5:
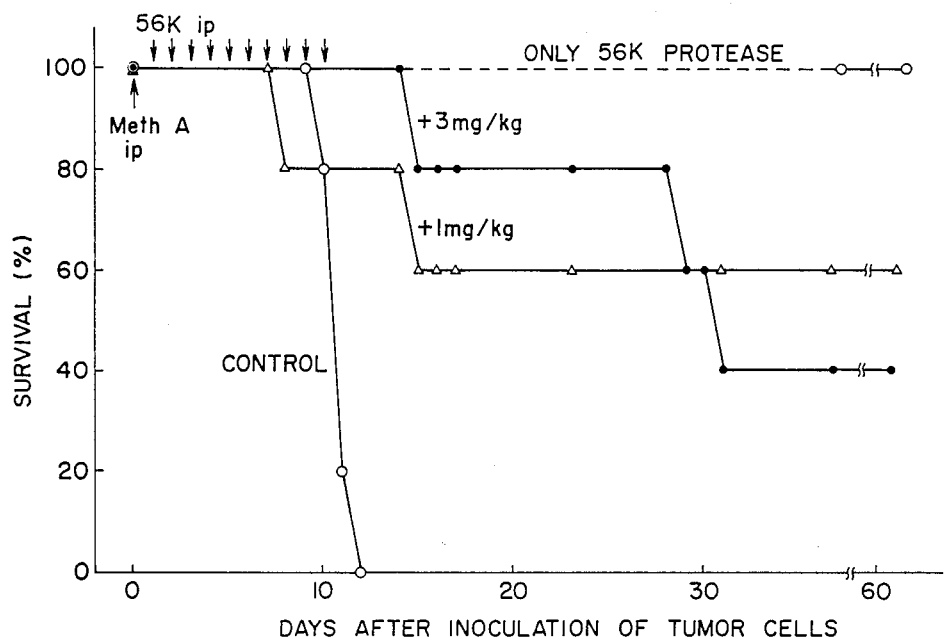
FIG. 5 shows anti-tumor actions of 56K protease against Meth A ascites peritoneal tumor cells, where arrow mark shows administration of 56K protease.

(2) Prolongation of life span in mice with Meth A tumor (ascites type):

$5 \times 10^5$ Meth A cells were injected into the peritoneal cavity of BALB/c mice, and at the 24th hour and thereafter, treatment with 56K protease was started, with a total 10 administrations (one administration each day). The results are shown in FIG. 5. As is obvious from FIG. 5, a remarkable survival rate was observed with administrations of 1 mg/kg and 3 mg/kg in contrast to the control.

(3) Growth suppressive effect on Meth A solid tumor by oral administration of 56K protease:

$2 \times 10^6$ Meth A tumor cells were subcutaneously inoculated into the back skin of mice, and a feed (50 g) containing 20 mg of 56K protease was given to one group of ten mice at the 24th hour and thereafter, whereas only normal feed was given to the control group of 10 mice to make a comparative study of tumor growth.

Average tumor sizes were compared 10 days after the start of feeding, and it was found that the group treated with 56K had an average tumor diameter of 7.7 cm, whereas the control group had an average tumor size of 8.9 cm, and thus there was obviously a significant difference (F determination: significant level 2.5%).

Test Example 4

Acute toxicity test of various proteases:

Various proteases (56K protease, Subtilisin, and Pronase) dissolved in physiological salt water were intravenously or intraperitoneally administered to one group of 10 ddY mice having body weights of 20 to 25 g, and the symptoms were observed over one week; $LD_{50}$ value were about 14 mg/kg with the administration of all the proteases.

As is obvious from the foregoing, it has been found that any of 56K protease, Subtilisin, Pronase, and neutral protease produced by Actinomyces has a remarkable anti-tumor action. Thus, practical application of anti-tumor agents containing these proteases as an effective component is highly promising.

In administration of these proteases into human bodies, effective treatment can be attained by direct administration into tumors or abdominal cavity, or by oral administration.

Administration dosage of these proteases depends on the size of the tumors, propagation speed, etc., but usually 10 μg to 1 mg of proteases is injected into tumor at one to several locations. Against an intraperitoneal tumor or disseminated tumor, usually 1 to 200 ml of a diluted enzyme solution is injected into the abdominal cavity.

In the oral administration, usually 1 mg to several grams thereof are administered at one time or in portions for one adult per day.

Powders, aqueous solution, granules, capsules, enteric coating, or medicinal oil or oil solutions can be used as medical administration forms, or pepsin inhibitor can be used together as a mixture to protect the proteases from attack of pepsin in the gastric-juice, which inactivates the proteases.

The present invention will be described in detail below, referring to Examples.

EXAMPLE 1

100 mg of 56K protease prepared in Preparatory Example 1 was dissolved in 10 ml of physiological saline, and the solution was aseptically filtered through a membrane filter. The filtrate was filled into a sterilized glass container freeze dried, and tightly sealed to make freeze dried powders for injection.

EXAMPLE 2

100 g of 56K protease powders prepared according to Example 1, 97 g of lactose, and 3 g of magnesium stearate were each weighed out and uniformly mixed. Then, 200 mg of the mixture was filled each in No. 2 gelatin capsules, and the capsules were subjected to enteric coating to make enteric-coated capsules.

EXAMPLE 3

200 mg of Subtilisin was dissolved in 10 ml of physiological saline, and the solution was aseptically filtered through a membrane filter. 10 ml of the filtrate was filled each into sterilized glass containers, freeze dried, and tightly sealed to make freeze dried powders for injection.

EXAMPLE 4

1 g of Subtilisin powders obtained according to Example 3, 84.5 g of crystal cellulose, 10 g of mannitol, 2.0 g of calcium carboxymethylcellulose, 1.0 g of magnesium stearate and 1.5 g of hardened oil were each weighed out, and uniformly mixed. The mixture was granulated by an extruder to make granules for oral administration.

EXAMPLE 5

500 mg of Pronase was dissolved in 10 ml of physiological salt water, and the solution was aseptically filtered through a membrane filter. 10 ml of the filtrate was filled each into sterilized glass containers, freeze dried, and tightly sealed to make freeze dried powders for injection.

EXAMPLE 6

1 g of Pronase powders obtained according to Example 5, 84.5 g of crystal cellulose, 10 g of lactose, 2 g of calcium carboxymethylcellulose, 1 g of magnesium stearate, and 1.5 g of stearic acid were uniformly mixed, and the mixture was converted into tablets each having a weight of 100 mg. The tablets were coated with an enteric coating agent to make enteric coated tablets.

Preparatory Examples, Test Examples and Examples of the present anti-tumor agents containing chemically modified proteases originating from microorganimms as an effective component will be given below:

Preparatory Example 2

Preparation of protease originating from *Bacillus sp.* (which will be hereinafter referred to as "AT protease"):

A medium containing 2% soluble starch, 1.5% soybean powder, 0.4% peptones, 0.2% yeast extract, 0.1% $KH_2PO_4$, 0.3% $K_2HPO_4$, 0.01% $MgSO_4 \cdot 7H_2O$, 0.02% $CaCl_2 \cdot 2H_2O$, and 1.0% $CaCO_3$ was sterilized in an autoclave at 121° C. for 20 minutes, and *Bacillus sp.* No. 36 FERM-BP No. 1152 was inoculated thereon, and cultured at 45° C. for 24 hours. After separation of the cells by centrifugation, crude enzyme powder was obtained by alcohol precipitation. The crude enzyme powder was dissolved in a 20 mM tris-hydrochloride buffer (pH 8.0) containing 2 mM calcium acetate and 1M ammonium sulfate, and the solution was passed through a column of Toyopeal HW 55 (tradename of Toyo Soda K.K., Japan), equilibrated with the same buffer as above in advance, to adsorb the protease. After washing with 20 mM tris-hydrochloride buffer (pH 8.0) containing 2 mM calcium acetate and 0.8M ammonium sulfate, the adsorbed protease was eluted with 20 mM tris-hydrochloride buffer (pH 8.0) containing 2 mM calcium acetate and 0.4M ammonium sulfate, and the eluate was dialyzed against 2 mM calcium acetate. The dialyzate was freeze dried, whereby a purified protease was obtained, which showed a single band upon SDS polyacrylamide electrophoresis using 12.5% acrylamide gel.

Furthermore, the enzyme was subjected to chemical modification by the present inventors according to various known methods, for example, disclosed in Marshal J et al: J. Biol. Chem. 251, 1081-1087 (1976). That is, the method is based on (1) coupling with saccharides e.g. dextran at molecular weight of 5,000-70,000 and dextran sulfate of molecular weight of 5,000 etc., (2) introduction of hydrophobic polymeric group such as polyalkylene glycol, preferably polyethylene or polypropylene glycol of molecular weight of 500-20,000 dalton, wherein the polymer is unsubstituted or substituted by alkoxy or alkyl groups, said alkoxy or alkyl group possessing less than 5 carbon atoms. And the polyalkylene glycol is activated in a conventional manner and conjugated to the amino groups of a protease, (3) alteration of protein surface electric charge, (4) conjugation with the low molecular weight anti-tumor agent, (5) formation of dimer or oligomer by crosslinking of protease molecules, (6) conjugation with synthetic polycations, (7) conjugation with synthetic polyanions, (8) combination of the above-mentioned procedures, etc.

Examples of chemical modification of proteases originating from microorganisms, used in the present invention will be given in detail below, referring to Preparatory Examples 3 to 13.

Preparatory Example 3

1 g of dextran (average molecular weight: about 10,000, made by Pharmacia AB, Sweden) was dissolved in 9 ml of deionized water, and 1 ml of 10% sodium metaperiodate was added thereto. The mixture was left standing in the dark, at 4° C. overnight to effect activation, and then 30% sodium bisulfite was added thereto in several portions to reduce the excess iodine. After disappearance of the iodine color, the mixture was thoroughly dialyzed against deionized water to remove the salts, and the dialyzate was freeze dried to obtain activated dextran. Then, 20 mg of the activated dextran powder was dissolved in 10 ml of 0.1M borate buffer together with 10 mg of purified AT protease, and the solution was subjected to reaction overnight. Unreacted substances were removed therefrom by gel filtration through a column of Sephacryl S-300 (made by Pharmacia AB, Sweden), and the conjugate obtained was dialyzed and freeze dried. The protease activity was measured by caseinolytic activity, and it was found that the activity yield was 63%.

Preparatory Example 4

100 mg of Dextran sulfate (molecular weight: about 5,000, Sigma Chemical Co.,) was dissolved in 47 ml of 0.4N NaOH, and 3 ml of epichlorohydrin was added thereto. The mixture was subjected to reaction at 40° C. for 2 hours with stirring. The reaction solution was neutralized with 1N HCl, and evaporated to dryness in an evaporator. Then, the residues were dissolved in 0.1M borate buffer (pH 9.0) containing 2 mM calcium acetate together with 10 mg of AT protease, and the solution was subjected to reaction at 4° C. overnight. The reaction product was filtered through a membrane filter having such a pore size as to cut off the substances having molecular weights of 10,000 to remove unreacted dextran sulfate. Then, the reaction product was subjected to SDS polyacrylamide electrophoresis to determine the molecular weight. It was found that the band of original AT protease (molecular weight: 37,500) had disappeared, and a band was detected in a higher range (40,000 to 45,000). The product was dialyzed against 2 mM calcium acetate$^{2+}$, and the dialysate was freeze dried.

Preparatory Example 5

20 g of monomethoxypolyethyleneglycol (M.W. 5,000) was dissolved in 100 ml of benzene, and 365 mg of cyanuric chloride was added thereto. The mixture was subjected to reaction at 80° C. for 44 hours, and activated polyethyleneglycol was obtained through precipitation by petroleum ether (the polyethylene glycol will be hereinafter referred to as "PEG"). Then, 30 mg of AT protease was dissolved in 15 ml of 0.1M borate buffer (pH 8), and 500 mg of activated PEG was added thereto. The mixture was subjected to reaction at 37° C. for one hour.

The reaction solution was subjected to gel filtration through a column of Sephacyl S-200 to collect fractions having molecular weights of 50,000 to 100,000, and the collected fractions were dialyzed and freeze dried, whereby 5 mg of a preparation was obtained. The protease activity yield was about 10%.

Preparatory Example 6

30 mg of 56K protease was dissolved in 2 ml of 0.8M NaHCO$_3$, and 10 mg of styrene-maleic anhydride copolymer (which will be hereinafter referred to as "SMA", molecular weight: 2,000) was added thereto. The mixture was subjected to reaction at 4° C. for 16 hours, followed by dialyzation against 0.1M borate buffer (pH 8.5), and the dialyzate was subjected to gel filtration through a column of Sephacyl S-200, whereby fractions having molecular weights of about 60,000 were collected. The collected fractions were dialyzed and freeze dried, whereby 5 mg of this preparation was obtained.

Preparatory Example 7

20 mg of AT protease was dissolved in 10 ml of 0.01M imidazole buffer, and 25 mg of succinic anhydride powder was slowly added. The mixture was subjected to reaction for 2 hours while keeping neutral pH with 1N NaOH. The reaction product was dialyzed against the same buffer as above, and the dialyzate was adsorbed through a column of DEAE-cellulose (made by Whatman Co.,), equilibrated with the same buffer. Then, the column was subjected to a linear gradient elution with 0-0.5M NaCl, whereby fractions eluted at a higher salt concentration (0.4M) than that for the original protease were collected. The collected fractions were dialyzed and freeze dried. The modified AT protease thus obtained had much excess negative electric charge on the surface of this succinylated enzyme.

Preparatory Example 8

20 mg of 56K protease described in Preparatory Example 1 was dissolved in 4 ml of 0.01M calcium acetate solution, and 5 ml of an aqueous 2M N,N-dimethylethylenediamine solution (pH 8), and then 1 ml of 1M water-soluble carbodiimide solution were added thereto. Then, the mixture was subjected to reaction at 4° C. overnight, and the reaction product was dialyzed against 2 mM calcium acetate solution. The dialyzate was freeze dried. By 7.5% polyacrylamide electrophoresis (pH 4.0), it was found that the band was shifted toward the cathode side rather than that of the original 56K protease, and the product had basic properties.

Preparatory Example 9

20 mg of AT protease was dissolved in 10 ml of 0.01M tris-HCl buffer containing 2 mM $Ca^{2+}$, and 170 μl of an ethanol solution containing 5 mg/ml of N-succinimidyl-(pyridyldithio) propionate (which will be hereinafter referred to as "SPDP") was added thereto in portions. The mixture was subjected to reaction at room temperature for 30 minutes, and the reaction product was desalted through a column of Sephadex G-25 (made by Phermacia AB, Sweden).

On the other hand, 13 mg of poly-L-lysine (molecular weight: about 47,000, from by Sigma Chemical Co. Ltd.) was treated in the same manner as above. Then, dithiothreitol was added to the AT protease solution treated with SPDP to make 0.1 M dithiothreitol, and the mixture was immediately desalted, and the thus obtained AT protease having a thiol group was mixed with SPDP poly-L-lysine. The mixture was subjected to reaction at 4° C. overnight, whereby poly-L-lysine bonded to AT protease through the disulfide bond was obtained. The unreacted substances were separated therefrom through a column of Sephacryl S-300, and the eluate was dialyzed and freeze dried.

Preparatory Example 10

56K protease disclosed in Preparatory Example 1, a low molecular weight anti-tumor agent methotrexate (which will be hereinafter referred to as "MTX"), and water-soluble carbodiimide in a ratio of 1:50:500 were subjected to reaction at overnight in 10 ml of 0.1M tris-hydrochloride buffer (pH 8.0), and then the reaction product was dialyzed against an aqueous 2 mM calcium acetate solution to remove the unreacted low molecular weight substances and salts. Then, the dialyzate was freeze dried. By UV spectral analysis, it was found that 4 molecules of MTX bonded to one molecule of the protease were obtained.

Preparatory Example 11

Reaction was carried out in the same manner as in Preparatory Example 10, using cytosine arabinoside (which will be hereinafter referred to as Ara-C) as a DNA polymerase inhibitor in place of the low molecular weight anti-tumor agent MTX used in Preparatory Example 10 to obtain AT protease bonded to cytosine aribinoside.

Preparatory Example 12

56K proteases themselves were subjected to intermolecular cross-linking through the disulfide bond by the SPDP disclosed in Preparatory Example 9. The reaction products were separated into dimers and unreacted monomers through a column of Sephacryl S-200, and only the dimer was dialyzed and freeze dried.

Preparatory Example 13

20 mg of 56K protease disclosed in Preparatory Example 1 was dissolved in 9.0 ml of 0.05M borate buffer (pH 9) containing 2 mM calcium acetate, and 1 ml of acetone was added thereto. 40 mg of $NaBH_4$ powders was added thereto in portions over one hour with stirring, while keeping $NaBH_4$ in the powdery state, and the reaction product was subjected to gel filtration through a column of Sephadex G-25 to remove unreacted low molecular weight substances, and the filtrate was freeze dried. As a result, the amino groups of protease were replaced with the isopropyl group to increase the hydrophobic properties and lower the isoelectric point (the shift of the isoelectric point was found to occur by 7.5% polyacrylamide electrophoresis).

The procedure for measuring the protease activity used in the present invention will be described below: To 1 ml of milk casein (1.5% W/V, 0.1M phosphate buffer, pH 8.0) as a substrate was added 1 ml of an enzyme solution (diluted with the same buffer), and the mixture was subjected to reaction at 37° C. for 30 minutes. Then, 2 ml of 0.4M trichloroacetic acid was added thereto to stop the reaction. Then, the reaction product was freed from the solidified, denatured protein by centrifuge, and the absorbancy of the supernatant at A 280 nm was measured. The activity unit was calculated according to the following equation:

$$\text{Increased A 280 nm value} \times 1/30 \times 1/\text{enzyme amount (mg)} = \text{unit/mg}$$

The anti-tumor action of the various chemically modified proteases obtained in the foregoing Preparatory Examples 3 to 13 are shown in Test Example 5, and the acute toxicity thereof in Test Example 6.

Test Example 5

$2.5 \times 10^6$ of B-16 melanoma cells/mouse were subcutaneously inoculated on the abdominal side of Cri:$BDF_1$ mice, and when tumor volume grew to about 200 $mm^3$ in 10 to 20 days thereafter, the respective chemically modified proteases, adjusted to the predetermined concentrations, were administered at one time. Dosages of administration of the modified proteases were determined in terms of the original protease activity, and grouped into three dosages, i.e., high dose (3.3 mg/ml), a medium dose (1.0 mg/ml), and low dose (0.33 mg/ml). Protease solutions of the respective concentrations were used in amounts of 0.1 ml per 150 $mm^3$ of tumor in accordance with the size of the solid tumor on mouse. Solvent for proteases was physiological saline for 56K protease and its modified product, and physiological saline contained 2 mM calcium acetate for AT protease and its modified product.

The tumor size was measured on the 1st day, 4th day, 7th day, and 10th day after the day 9 of the drug administration (days). The size was measured by its volume (=(long diameter/2×short diameter/2)×π×height; in $mm^3$ as unit).

The results are shown in Table 3. The criteria of the positive effect were based on values obtained by measuring tumor volume after administration of the individual modified proteases, using the value of the 4th day and 7th day. Smaller values show increasing anti-tumor activity of modified protease, as compared with the original protease as unit.

TABLE 3

| Tumor volumic increment | Relative change* |
|---|---|
| 56K | 1.00 |
| 56K-PEG | 0.80 |
| 56K-SMA | 0.71 |
| 56K-succinate | 0.72 |
| 56K-methotrexate | 0.63 |
| 56K-dimethylethylenediamine | 0.84 |
| 56K-alkylated | 0.82 |
| 56K-dimer | 0.92 |
| AT | 1.00 |
| AT-dextran sulfate | 0.74 |
| AT-PEG | 0.31 |
| AT-SMA | 0.58 |
| AT-succinate | 0.63 |
| AT-dimethylethylenediamine | 0.82 |
| AT-methotrexate | 0.56 |
| AT-cytosine arabinoside | 0.71 |
| AT-dimer | 0.76 |
| AT-dextran | 0.53 |
| Control | 3.80 |

*Value of 1.0 indicates relative tumor volume to day 0. In Table 3, 56K stands for 56K protease, and AT for AT protease, and control means tumor without protease injection.

As is obvious from Table 3, the chemically modified proteases originating from microorganisms have a stronger anti-tumor action than the original protease.

Test Example 6

Acute toxicity test of various chemically modified proteases:

Various chemically modified proteases dissolved in physiological saline or physiological saline containing 2 mM calcium acetate were administered intravenously or intraperitoneally into a group of ten ddY mice having body weights of 20 to 25 g, and the symptoms were observed over one week, and LD50 values were about 14 mg/kg with the administration of all the proteases.

As is obvious from the foregoing, it has been found that the chemically modified proteases originating from microorganisms had a remarkable anti-tumor action. Thus, practical application of anti-tumor agents containing these chemically modified proteases originating from microorganisms as an effective component is highly promising.

Administration of these chemically modified proteases originating from microorganisms into human subjects may be achieved by direct administration into tumor tissue or abdominal cavity, or by oral administration or intravenously or, more preferably, intraarterially.

Administration dosage of these chemically modified proteases originating from microorganisms depend on the size of tumors, speed of multiplication, etc., but usually 10 µg to 1 mg of proteases is injected into tumor at one or several locations. Against the intracelial peritoneum tumor or disseminated intracelial tumor, usually 1 to 200 ml of a diluted solution of chemically modified protease originating from microorganisms is injected into the abdominal cavity.

In oral administration, usually 1 mg to several grams thereof are administered at one time or in portions for one adult per day.

Powders, aqueous solution, granules, capsules, enteric coating, or medicinal oil, or oil solutions can be used as medical dose forms, or a pepsin inhibitor can be used together as a mixture to protect the chemically modified proteases originating from microorganisms from attack of pepsin in the gastric juice, which inactivates the chemically modified proteases.

EXAMPLE 7

100 mg of PEG-modified AT protease prepared in Preparatory Example 5 was dissolved in 10 ml of physiological saline containing 2 mM calcium acetate, and the solution was aspectically filtered through a membrane filter. The filtrate was filled into a sterilized glass container, freeze dried, and tightly sealed to make freeze dried powders for injection.

EXAMPLE 8

100 g of PEG-modified AT protease powders obtained in Example 7, 97 g of lactose, and 3 g of magnesium stearate were each weighed out and uniformly mixed. Then, 200 mg of the mixture was filled each in No. 2 gelatin capsules, and the capsules were subjected to enteric coating to make enteric-coated capsules.

EXAMPLE 9

200 mg of dextran-conjugated AT protease prepared in Preparatory Example 3 was dissolved in 10 ml of physiological saline, and the solution was aseptically filtered through a membrane filter. 10 ml of the filtrate was filled each into sterilized glass containers, freeze dried, and tightly sealed to make freeze dried powders for injection.

EXAMPLE 10

1 g of dextran-conjugated AT protease prepared in Preparatory Example 3, 84.5 g of crystal cellulose, 10 g of mannitol, 2.0 g of calcium carboxymethylcellulose, 1.0 g of magnesium sterate, and 1.5 g hardened oil were each weighed out, and uniformly mixed. The mixture was granulated by an extruder to make granules for oral administration.

EXAMPLE 11

500 mg of methotrexate-conjugated 56K protease prepared in Preparatory Example 10 was dissolved in 10 ml of physiological saline, and the solution was aseptically filtered through a membrane filter. 10 ml of the filtrate was filled each into sterilized glass containers, freeze dried, and tightly sealed to make freeze dried powders for injection.

EXAMPLE 12

1 g of methotrexate-conjugated 56K protease powders obtained in Example 11, 84.5 g of crystal cellulose, 10 g of lactose, 2 g of calcium carboxymethylcellulose, 1 g of magnesium stearate, and 1.5 g of stearic acid were uniformly mixed, and the mixture was converted into tablets each having a weight of 100 mg. The tablets were coated with an enteric agent to make enteric coated tablets.

The present anti-tumor agents containing protease originating from microorganisms as an effective component and the present anti-tumor agents containing chemically modified protease originating from microorganisms as an effective component have a pharmaceutical activity of good duration and a low toxicity to the normal cells as features; and the latter can evade immunological reaction which seems to occur with frequent or repeated administration.

We claim:

1. Method for treating a tumor in a mammal which comprises directly administering into the tumor of said mammal an effective anti-tumor amount of proteases produced from a source, said source selected from the group consisting of *Serratia marcescens, Bacillus sp.* and *Streptomyces griseus,* wherein said protease is other than an acid protease.

2. Method for treating a tumor in a mammal which comprises directly administering into the tumor of said mammal an effective anti-tumor amount of a protease selected from the group consisting of *Serratia marcescens, Bacillus sp.* and *Streptomyces griseus,* wherein said protease is other than an acid protease, and said protease is chemically modified by one of the following procedures:

(a) coupling with a saccharide,
(b) introduction of a hydrophobic polymeric group,
(c) alteration of electric charge of the protein surface,
(d) conjugation with a low molecular weight anti-tumor agent of molecular weight less than 2,000,
(e) formation of dimer of oligomer by cross-linking of protease molecules,
(f) conjugation with a synthetic polycation,
(g) conjugation with a synthetic polyanion, and
(h) combination of the above-mentioned procedures.

3. Method according to claim 1, wherein the effective anti-tumor amount of protease is from about 30 $\mu$g to 300 $\mu$g/kg.

4. Method according to claim 2, wherein the effective anti-tumor amount of proteases is from about 30 $\mu$g to 5 $\mu$g/kg.

* * * * *